(12) United States Patent
Feilkas

(10) Patent No.: US 9,002,432 B2
(45) Date of Patent: Apr. 7, 2015

(54) METHOD AND DEVICE FOR CALIBRATING A MEDICAL INSTRUMENT

(75) Inventor: Thomas Feilkas, Grafing (DE)

(73) Assignee: Brainlab AG, Feldkirchen (DE)

( * ) Notice: Subject to any disclaimer, the term of this patent is extended or adjusted under 35 U.S.C. 154(b) by 2915 days.

(21) Appl. No.: 11/274,929

(22) Filed: Nov. 15, 2005

(65) Prior Publication Data

US 2006/0173356 A1 Aug. 3, 2006

Related U.S. Application Data

(60) Provisional application No. 60/694,844, filed on Jun. 29, 2005.

(30) Foreign Application Priority Data

Nov. 15, 2004 (EP) ..................................... 04027075
Jun. 17, 2005 (EP) ..................................... 05013163

(51) Int. Cl.
*A61B 5/05* (2006.01)
*A61B 5/06* (2006.01)
*A61B 17/28* (2006.01)
*A61B 19/00* (2006.01)
*A61B 17/00* (2006.01)

(52) U.S. Cl.
CPC . *A61B 5/06* (2013.01); *A61B 17/28* (2013.01); *A61B 19/50* (2013.01); *A61B 19/52* (2013.01); *A61B 19/5212* (2013.01); *A61B 19/5244* (2013.01); *A61B 2017/00725* (2013.01); *A61B 2019/502* (2013.01); *A61B 2019/5255* (2013.01); *A61B 2019/5483* (2013.01)

(58) Field of Classification Search
USPC .................................. 600/424, 407, 410, 160
See application file for complete search history.

(56) References Cited

U.S. PATENT DOCUMENTS

| | | | |
|---|---|---|---|
| 6,428,547 B1 | 8/2002 | Vilsmeier et al. | |
| 6,724,922 B1 | 4/2004 | Vilsmeier | |
| 2001/0051761 A1 | 12/2001 | Khadem | |
| 2003/0112922 A1* | 6/2003 | Burdette et al. | 378/65 |
| 2004/0169673 A1 | 9/2004 | Crampe et al. | |

FOREIGN PATENT DOCUMENTS

| | | |
|---|---|---|
| DE | 199 44 516 A1 | 4/2001 |
| EP | 1 369 090 A1 | 12/2003 |
| EP | 1 413 258 A1 | 4/2004 |

OTHER PUBLICATIONS

Colchester A C F et al., "Development and preliminary evaluation of VISLAN, a surgical planning and guidance system using intra-operative video imaging", Medical Image Analysis, Oxford University Press, Oxford, GB, Bd. 1, Nr. 1, 1996, Seiten 73-90, XP002322964.

* cited by examiner

*Primary Examiner* — Joel Lamprecht
(74) *Attorney, Agent, or Firm* — Tucker Ellis LLP

(57) ABSTRACT

A system and method for calibrating an object having at least one marker attached thereto, wherein a spatial position of the object is ascertained based on the at least one marker, and an outline, view or geometry of the object is optically detected from at least one side. The detected outline, view or geometry is compared with corresponding outlines, views or geometries of stored pre-calibration data of the object, said pre-calibration data representing a model of the object.

23 Claims, 6 Drawing Sheets

METHOD AND DEVICE FOR CALIBRATING A MEDICAL INSTRUMENT

RELATED APPLICATION DATA

This application claims priority of U.S. Provisional Application No. 60/694,844 filed on Jun. 29, 2005, which is incorporated herein by reference in its entirety.

FIELD OF THE INVENTION

The present invention relates to a device and a method for calibrating an instrument and, more particularly, to calibrating a medical instrument and detecting a geometric structure or configuration of the instrument.

BACKGROUND OF THE INVENTION

Medical instruments employed in image-guided surgery must be calibrated, verified and/or validated prior to use. In other words, the precise dimensions, configuration or arrangement of the instrument must be known. Otherwise, healthy tissue that lies next to target tissue may be inadvertently operated on due to an unknown or deformed instrument, e.g., due to instrument bending.

A device and a method for calibrating a bent element are known from EP 1 413 258 A1, wherein the bent element is connected to a navigation element. The element also is attached to a calibration device, and the element is moved until the element is calibrated.

Navigationally calibrating medical instruments or implants is known from EP 1 369 090 A1, wherein a spatial position of the instrument or implant is ascertained by means of a medical navigation system. The position of the instrument or implant then can be ascertained relative to anatomical data, wherein the spatial orientation of a multi-dimensionally designed, functional section of the instrument or implant also can be ascertained.

U.S. Pat. No. 6,428,547 B1 describes recognizing the shape of a treatment apparatus, wherein the treatment apparatus is referenced in a computer-controlled, camera-assisted navigation system by means of a marker array attached to the treatment apparatus. Projections of the treatment apparatus are detected by means of x-ray recordings, and the shape of the treatment apparatus is assigned to the projections in the navigation system based on the position of the marker array in the projections.

A verification method for positions in camera images is known from U.S. Pat. No. 6,724,922 B1.

DE 199 44 516 A1 describes a method for detecting the shape of an object, wherein a camera image of the object is produced and an outline of the object is detected in a first plane by an evaluation unit connected to the camera. A focusing distance of the camera then is altered and an outline of the object is detected by the evaluation unit in a second plane. These steps are repeated until a sufficient number of outlines have been detected, such that the spatial shape of the object can be established.

SUMMARY OF THE INVENTION

A method for calibrating, verifying and/or validating an instrument or implant for medical use (referred to below as an instrument) is provided. At least one marker and preferably three markers (e.g., a reference star) or a number of markers having a known geometry (e.g., fixed or variable in accordance with the configuration of the instrument) can be attached to the instrument, wherein the spatial position of the instrument can be ascertained based on the markers via a navigation system using a known method. The markers can be formed as reflecting surfaces or spheres, for example. A camera that can detect infrared light emitted or reflected from the markers can be provided for detecting the position of the instrument. The camera preferably is calibrated and the spatial position of the camera may be unknown, known or defined. Furthermore, the geometry (e.g., one or more views, mappings or outlines of the instrument from one or more various directions) can be optically detected via a camera, wherein the camera can be the same camera used for detecting the position of the markers. The camera also may be a second camera (e.g., different from the first camera), wherein images can be recorded in the visible spectral range.

The geometry or calibration data of the instrument can be stored in software (e.g., in a table or database) and/or in a computer, such that the three-dimensional representation of the instrument can be archived in the database. These stored, so-called pre-calibration data can be compared with the geometry of the instrument detected by the camera (e.g., the optically detected data) to establish whether the optically detected data representing the actual geometry or form of the instrument match the pre-calibration data. Thus, so-called tracking data and a camera image data can be assigned, wherein if the camera image data match the pre-calibration data, the instrument may be said to be calibrated, verified and/or validated. If a difference or deviation from the pre-calibration data is established, however, an error message can be generated, e.g., the instrument requires calibration, or the pre-calibration data, which may be used for subsequent navigation, can be adapted to the optically detected data. Preferably, the respective views or outlines of the instrument model that correspond to the orientation or position of the actual instrument relative to the camera, as measured via the markers, can be calculated from a three-dimensional data model or software model of the instrument.

Assuming that the image calculated by the computer based on the detected spatial position of the instrument (known as a three-dimensional model) and the knowledge of the calibration of the video camera is the representation, view or model of the environment and/or instrument by the computer or software, and that the video input data captured by a camera show the real or actual environment (e.g., an actual instrument), then if the video camera is precisely calibrated (e.g., it has a known position, orientation and detection range) and if a medical instrument is registered or calibrated, the image calculated by the computer for a pre-calibrated instrument can precisely coincide with the image that is obtained at the video input. If this is not the case, either the calibration or the adjustment of the camera may be faulty or the instrument may not correspond to the pre-calibration data (e.g., because the instrument has become bent due to regular use). Assuming that the calibration of the camera is correct throughout the method, then instruments for which there are pre-calibration data can be reliably verified using the calibrated space, which can be detected by the camera.

The data, which can be stored in a computer, for example, can define the geometry and possible degrees of freedom of the instrument. The data can be stored in a database, for example, as pre-calibration data (e.g., as a description of the three-dimensional object for a navigation system). Further, the data can represent a three-dimensional model that describes the precise shape of an object or instrument and the position of each marker or reference array on the object or instrument. The navigation system or computer can represent the three-dimensional model as the instrument the surgeon is using. The description of the pre-calibrated instrument can comprise information as to which areas or functional locations of the instrument that should be verified. Equally, information can be stored as pre-calibration data using possible shapes that the instrument can assume, such as, for example, information relating to joints that may be present and possible movements of the joints, or as general information relating to possible alterations or degrees of freedom of the instrument.

A calibrated video signal may be an input obtained from a standard video camera, the properties or parameters of which (e.g., the position and/or the detection function of the camera) can be determined and calculated for a so-called "virtual camera". This virtual camera can be used by the computer to calculate images based on three-dimensional objects (e.g., by projecting in the detection direction of the actual camera), which match the views or objects actually present or detected. For example, if the video camera is directed onto a cube-shaped object having known dimensions, the position of the cube-shaped object in three-dimensional space can be determined based on the image information, provided the camera space has been calibrated. Additional information can then be inserted into the video image recorded by the camera, for example, such that this additional information (e.g., a virtual representation of the instrument to be verified) appears to be a part of the scene recorded by the camera.

The calibrated video signal can be used to verify and validate pre-calibrated instruments, wherein no other object (e.g., a bearing surface) is required for calibration, such that the surgeon's work area is not impeded by an additional object or instrument. Contact-free verification may be performed by holding the instrument to be calibrated such that the video camera can detect at least an outline or can record a view of the object from at least one side, wherein a downstream software, such as the navigation system, for example, can automatically determine the correctness of the detected shape by comparing it with the pre-calibration data. If an instrument having a more complex shape is to be calibrated, the instrument may be moved or turned to record a number of views of the object using the camera, wherein software can provide a corresponding instruction for moving the instrument.

Further, the method can ensure that only calibrated instruments or implants are used for surgical procedures, since if the shape of an instrument deviates from the pre-calibration data, an error message can be output or the navigation system may not enable navigation due to detection of a faulty or incorrect instrument. Since it is no longer necessary to attach an instrument to a reference surface to calibrate the instrument, the method also simplifies handling of instruments that are to be kept sterile.

Although a single view may be used, it is preferable that at least two or more lateral views of the instrument are detected by the optical camera, wherein the instrument can be turned, shifted or rotated in the viewing range of the camera. Preferably, the visibility of certain points, such as the tip of an instrument, for example, can be checked or verified. To this end, it is possible to check whether specific points defined in the pre-calibration data, such as corner points, edges or tips of the instrument, for example, also are visible or concealed in the optically detected recording. If concealed, for example, a signal can be provided to indicate to the user that the concealed instrument should be held in the camera's line of view.

It is possible for only certain areas (e.g., corner points, edges, a tip or functional surfaces) of the instrument that are characteristic of or relevant to the function of the instrument to be checked against the pre-calibration data, wherein information relating to this checking procedure can be archived in software and in the pre-calibration data, for example.

In general, the pre-calibration data can include information regarding the geometry, the dimensions, the spatial arrangement of combinable elements (e.g., an instrument with exchangeable tips or an instrument for placing implants in connection with the selected implant), and/or regarding possible degrees of freedom (e.g., joints or possible deformations) of the instrument. By using the pre-calibration data, the configuration or current condition of an adjustable or deformable instrument can be recognized, and this information can be subsequently used on the actual configuration of the instrument (e.g., within the scope of supporting the treatment or for a surgical incision by means of image-guided surgery).

By comparing the image data detected by a camera and the pre-calibration data, it is possible to check whether an instrument is within a given specification, for example, which can be indicated in the pre-calibration data as a tolerance relating to dimensions of the instrument. If it is established that an instrument exceeds a tolerance limit, a corresponding message can be output, for example.

It is further possible for the data recorded by the camera with respect to the actual condition or the configuration of the instrument to be used to adapt or modify the pre-calibration data, such that the data ascertained by means of the camera with respect to the actual configuration of an instrument can be made available to the navigation system, for example, to precisely navigate said instrument.

It is possible for an instrument corresponding to the pre-calibration data and/or an instrument actually detected by the camera to be displayed, for example, on a screen, wherein both instruments, i.e., the actual and virtual instrument, are also simultaneously mapped next to or on top of each other, and displayed as a so-called overlapping or superimposed image, for example. It is then possible to compare characteristic points, such as corners and/or edges, for example, to establish whether the actual instrument matches or deviates from the virtual instrument in accordance with the pre-calibration data.

The camera for detecting the instrument is preferably calibrated. To this end, an optical design such as, for example, a chess or checker board or an object having known dimensions can be held in front of the camera such that on the basis of the image data captured by the camera, the dimensions of an object within the viewing range of the camera can be optionally ascertained using navigation data.

In accordance with another aspect, the invention provides a computer program which, when loaded onto a computer or running on a computer, carries out one or more of the method steps described above. The program can include program sections for evaluating image data detected by an optical camera such that dimensions or the geometry of a visible range of the instrument can optionally be determined using navigation data, wherein the optically captured data can be compared with pre-calibration data.

The invention further provides a program storage medium or computer program product comprising such a program.

The invention further provides a device for calibrating an instrument that can be used medically. At least one marker or reference star can be attached to the instrument, said device including a computing unit and a memory connected to the computing unit. Pre-calibration data of at least one medical instrument can be archived in the memory. At least one camera also can be provided, wherein the camera can detect the markers attached to the instrument, and the camera can be connected to the computing unit that can ascertain the spatial position of the instrument on the basis of the detected marker image data and optionally on the basis of the pre-calibration data. The device also can include a camera for detecting the instrument itself or the geometry or dimensions of certain parts of the instrument, wherein the camera likewise can be connected to the computing unit such that a comparison can be made in the computing unit between the instrument data optically detected by the camera and the pre-calibration data archived in the memory. The camera for detecting the marker positions can be identical to the camera for optically detecting the instrument. It is equally possible for two different cameras or camera systems to be provided, for example, to detect the position of the markers and thus track the instrument connected to the markers with one camera, and to detect the instrument itself or its dimensions with the other camera.

It is possible for the camera used for optically detecting the instrument to itself have one or more markers attached to it, said markers being detected by the other camera, such that the spatial position of the camera connected to the markers can be ascertained and, based on the spatial position the direction of view onto the medical instrument detected by this camera can be calculated, e.g., the optically detected image data can be correlated with the positional data of the instrument, detected on the basis of the markers.

The device preferably comprises an image output unit, such as an LCD screen, for example, on which an instrument can be represented in accordance with the pre-calibration data, together with an image of the instrument detected by the camera. The invention further provides a system comprising a device as described above and an instrument to which at least one marker is attached.

The forgoing and other features and embodiments of the invention are hereinafter discussed with reference to the drawings.

DETAILED DESCRIPTION

Figure 1:
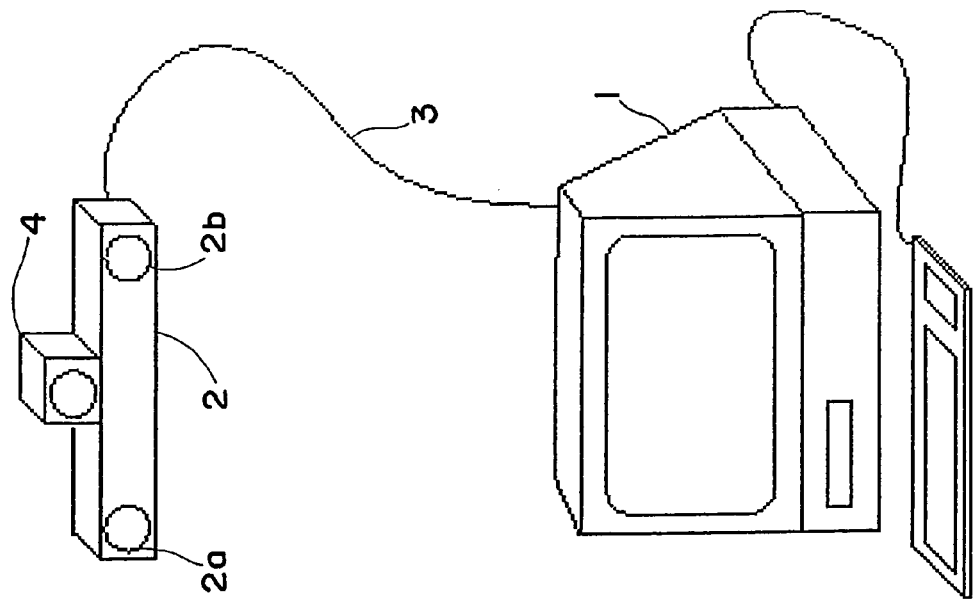
FIG. 1 illustrates a first exemplary device in accordance with the invention.
Figure 1:
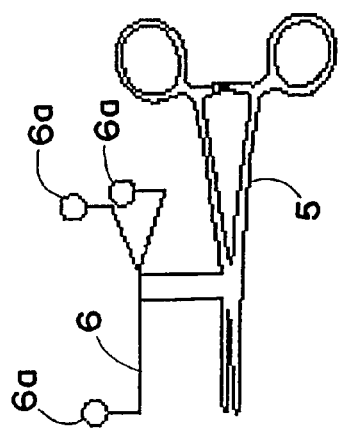

FIG. 1 shows a first exemplary system, wherein a computational unit 1 is coupled to an optical camera 4 and an optical tracking system 2 via a data lead, such as a cable 3 or a wireless radio (not shown). A reference star 6, which includes three markers 6a, is attached to a medical instrument 5. The medical instrument may be any medical instrument, and in the present example is a pair of scissors.

The optical tracking system 2 includes two infrared cameras 2a and 2b that can detect light signals reflected by the three markers 6a of the reference star 6, so as to detect the position of the medical instrument 5. Further, the video camera 4 is in a fixed position relative to the tracking or camera system 2. The data of the reference star 6 captured by the optical tracking system 2, together with the data of the instrument 5 captured by the video camera 4, are sent to the computing unit 1 and evaluated as described below with reference to FIGS. 3 and 4.

Since the position of the video camera 4 is fixed relative to the optical tracking system 2, the current spatial position of the video camera 4 is known and therefore need not be calculated. Thus, the current position of the video camera 4 is more precise when compared to a non-fixed video camera, since measurements made by the optical tracking system 2, which include a certain degree of imprecision, are not performed to determine the location of the optical camera 4.

By calibrating the video camera 4, information for a "virtual camera" is obtained. However, this is only valid for the current position of the video camera 4 relative to the tracking system 2. If the position of the video camera 4 is fixed as shown in FIG. 1, the calibration is maintained. If the video camera 4 is detached, however, as shown in FIG. 2, the current position of the video camera 4 is additionally determined to enable the position of the tracked instruments 5 to be connected to the "virtual camera".

Figure 2:
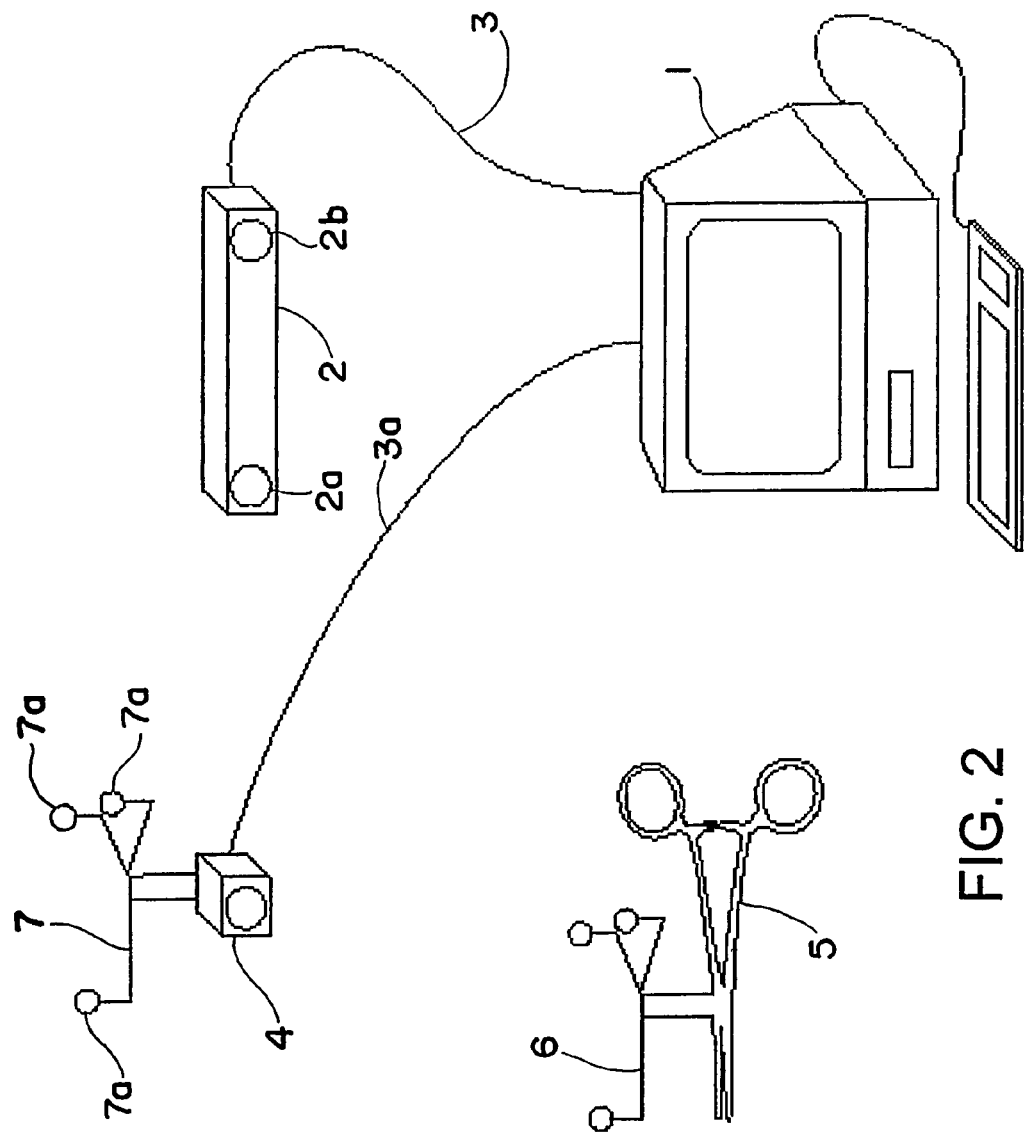
FIG. 2 illustrates a second exemplary device in accordance with the invention.

FIG. 2 shows another exemplary system, wherein the optical camera 4 is detached from the optical tracking system 2. Further, the optical camera 4 is connected to the computing unit 1 via a separate data connection, such as for example a cable 3a. Such an arrangement enables instruments to be detected more flexibly by the video camera 4, since the video camera 4 can be positioned independently of the tracking system 2. To this end, the distance between the instrument 5 and the video camera 4 is ascertained based on the coordinate system of the video camera 4, to enable the image data detected by the video camera 4 to be evaluated and the dimensions or the geometry of the instrument 5 to be ascertained from the data. Since the video camera 4 is connected to a reference star 7, the spatial position of the video camera 4 can be calculated based on the position of the reference star 7. Thus, the relative position between the video camera 4 and the instrument 5 also can be calculated, e.g., by determining the spatial position of the instrument 5 as detected by the tracking system 2 relative to the spatial position of the camera 4 as detected by the tracking system 2.

Figure 3:
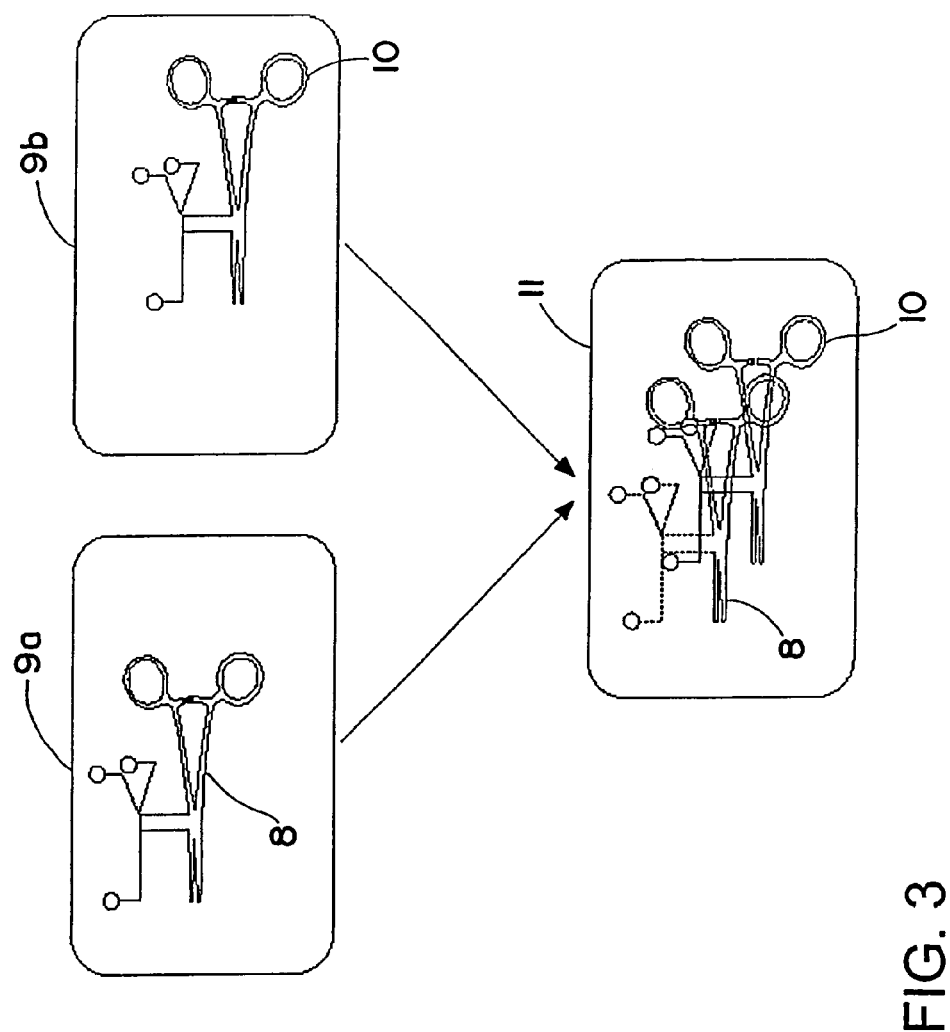
FIG. 3 illustrates the principle of superimposing a virtual instrument image and a detected instrument image.

FIG. 3 shows the principle of superimposing the video of the pre-calibration data image onto an actual image 8 detected by the video camera 4. In a video recording 9a, the actual image 8 of the instrument 5 is shown in front of the video camera 4. The computational unit 1 calculates a similar image 9b based on the positional information of the instrument 5 calculated by the tracking system 2 and the calibration of the video camera 4. This image 9b contains a computer-generated version of the representation of the instrument 10. These two images 9a and 9b are used to generate a superimposed image 11 in which both views of the instrument 8 and 10 are represented on top of each other. If the instrument 5 corresponds to the specifications by the pre-calibration data, the two images 8 and 10 can be completely superimposed. If, however, the instrument 5 deviates from the specification given by the pre-calibration data, differences between the actual image 8 and the computer generated image 10 are shown, enabling the precision of the instrument 5 to be verified.

Figure 4:
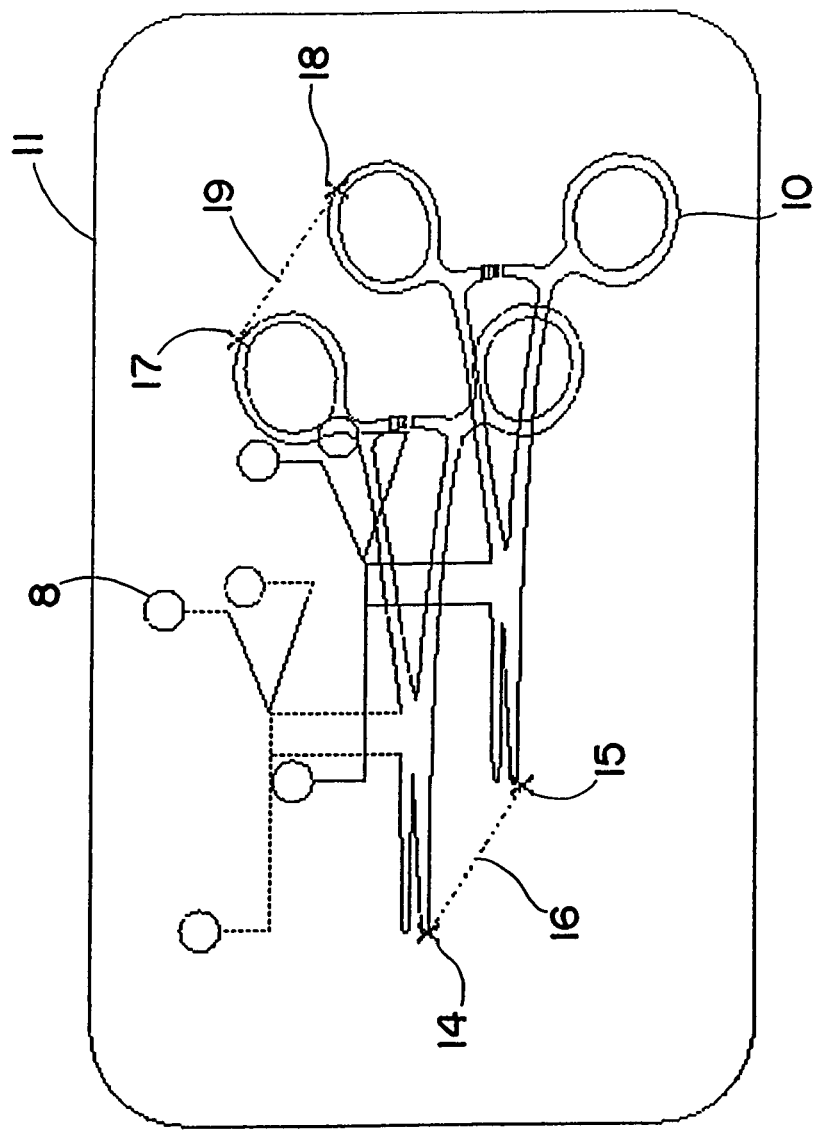
FIG. 4 illustrates an error between superimposed images of the instruments.

FIG. 4 shows an enlarged representation of the superimposed image 11 shown in FIG. 3, wherein the actual image 8 and the computer-generated image 10 do not completely align up to one another (e.g., they are not in the same location in the superimposed image 11). In order to obtain a direct superimposition or comparison of the images 8 and 10, corresponding corner points 14 and 15 or 17 and 18 of the images 8 and 10 can be used, and the differences 16 and 19 between the corresponding corner points can be calculated. If a number of differences with respect to corresponding corner points or edges are calculated, then it is possible to ascertain the preciseness in which the two images 8 and 10 match.

It is possible to pre-define specific corners in a model or in the pre-calibration data to enable a comparison of the objects, such that the visibility of certain functional elements, points or surfaces, for example, also can be checked (e.g., the visibility of a tip of the instrument 5 in the video image). In addition to or instead of the corner points, it is equally possible to compare lines, curves or shapes.

If more than one view of the instrument 5 is used, the position of the corner points 14 and 17 can be determined in three-dimensional space. For the points 15 and 18, these positions are known from the pre-calibration data. The exact deviation of the instrument 5 from the pre-calibration data can thus be calculated.

Alternatively, it would be possible to proceed in a similar way via CT fluoro-matching, which attempts to match a known shape of an object to one or more video images in which the object is shown. This would enable a total value of the difference or error between the position of the instrument, as detected by the video camera, and the position of the instrument, as calculated by the computer based on the tracking information, to be ascertained. This comparison would enable detection of registration errors.

Figure 5:
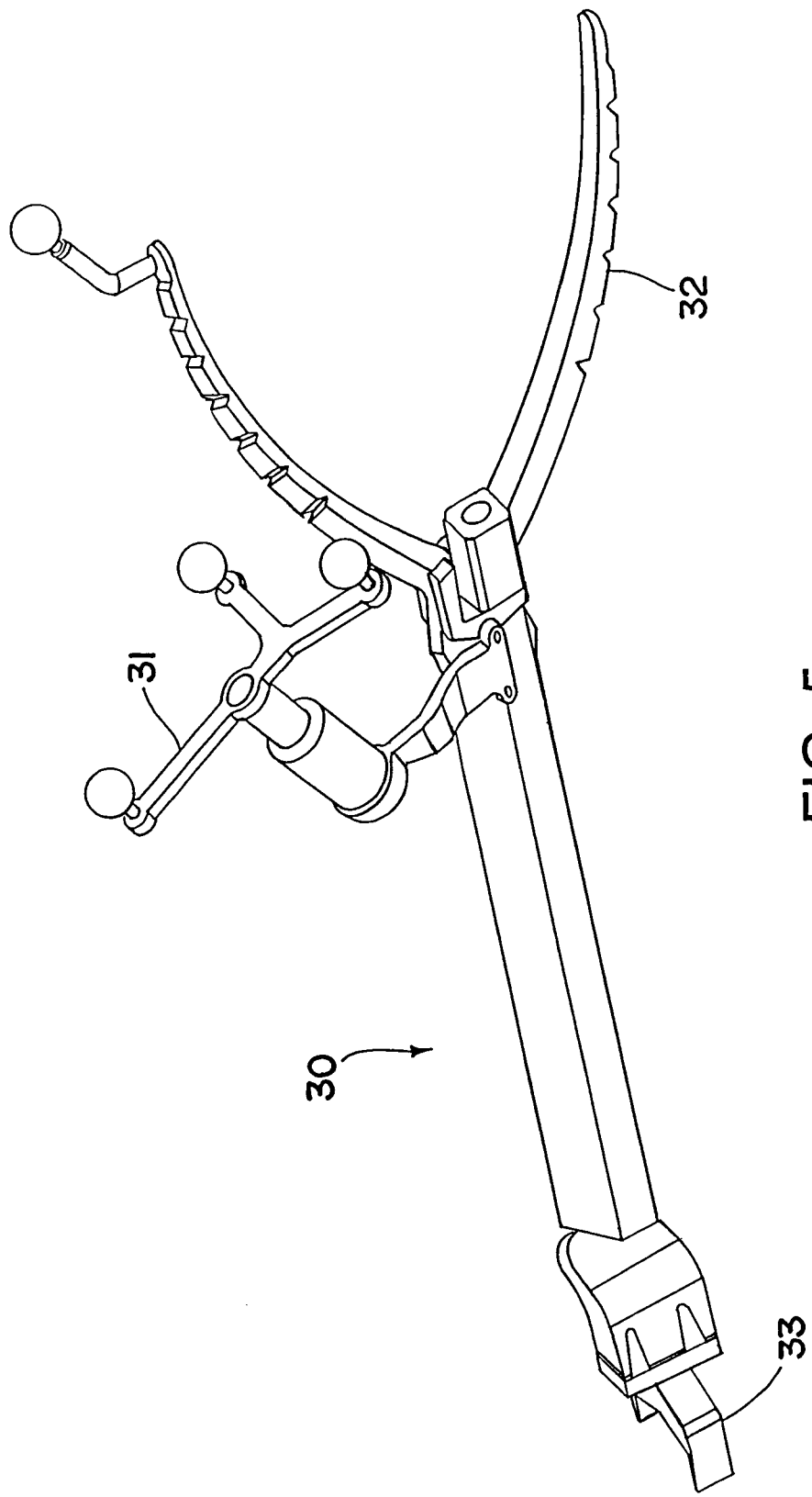
FIG. 5 illustrates a top view of an exemplary spreader for the navigated insertion of intervertebral discs.
Figure 6:
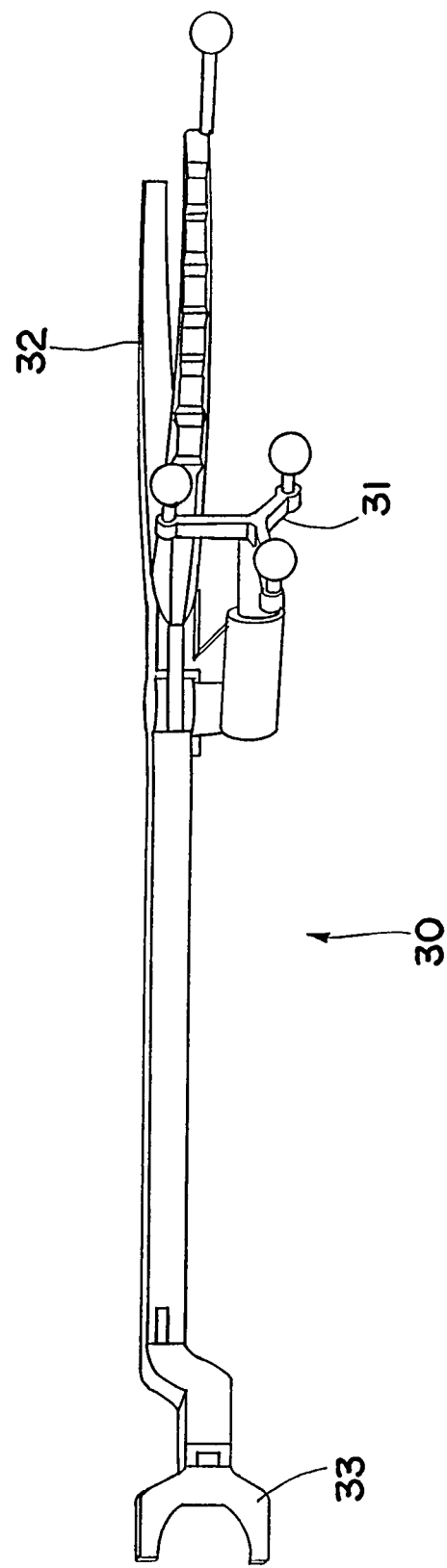
FIG. 6 illustrates a lateral view onto the spreader of FIG. 5.

FIGS. 5 and 6 show a spreader 30 which enables the navigated insertion of intervertebral disc implants. When using a spreader, it is important to ascertain the distance between the tip of the spreader 30 and the reference star 31 attached to the spreader 30, to enable exact positioning of the intervertebral disc implant. If the grips 32 of the spreader 30 are moved, then, due to the mechanical coupling between the spreader grips 32 and the pincer 33, the pincer 33 moves such that based the aperture angle of the grips 32, it is possible to establish the movement of the pincer 33 at the front end of the spreader 30, e.g., how far the vertebrae abutting the pincer 33 have been spread apart.

The spreader shown in FIGS. 5 and 6 can be calibrated by the device and the method described herein, such that it is possible to recognize whether the spreader matches the pre-calibration data. For example, it can be determined whether the spreader still matches the pre-calibration data during the application of a significant mechanical load on the front side of the spreader, whether a movement of the spreader grips 32 leads to a desired spreading of the pincer 33, or whether the spreader 30 has to be recalibrated.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for calibrating a medical instrument, comprising:
   optically detecting via an image capture device certain areas of the medical instrument from at least one side;
   comparing, with computer assistance, the detected certain areas with corresponding stored pre-calibration data of the medical instrument, said pre-calibration data representing data relevant to the function of the medical instrument; and
   ascertaining, with computer assistance, whether the medical instrument is calibrated based on the comparison.

2. The method according to claim 1, further comprising performing the method without contact from calibration instruments.

3. The method according to claim 1, wherein the medical instrument is not attached to a reference surface.

4. The method according to claim 1, wherein optically detecting includes optically detecting the medical instrument from a number of directions using a number of lateral views.

5. The method according to claim 1, further comprising checking pre-defined positions of the medical instrument to determine whether the pre-defined positions are optically detectable.

6. The method according to claim 1, wherein comparing certain areas includes comparing one or more tips, edges and/or functional surfaces of the medical instrument with the pre-calibration data.

7. The method according to claim 1, wherein the pre-calibration data includes information relating to the geometry, dimensions, joints, degrees of freedom and/or possible deformations of the medical instrument.

8. The method according to claim 1, further comprising ascertaining, after comparison with the pre-calibration data, a current configuration of the medical instrument from the optically detected medical instrument data.

9. The method according to claim 1, wherein comparing includes ascertaining whether the medical instrument is within a predetermined specification as defined in the pre-calibration data.

10. The method according to claim 1, further comprising using the optically detected data for navigation of the medical instrument when the optically detected data and the pre-calibration data deviate from one another beyond a predetermined threshold.

11. The method according to claim 1, further comprising optically displaying the optically detected data together with a medical instrument image calculated from the pre-calibration data.

12. The method according to claim 11, further comprising generating a superimposed image using the optically detected data and the calculated medical instrument image.

13. The method according to claim 1, further comprising calibrating the image capture device prior to optically detecting the medical instrument.

14. The method according to claim 10, wherein calibrating includes providing a known calibration object having a known design in a viewing range of the image capture device.

15. A non-transitory computer readable medium comprising computer executable instructions adapted to perform the method according to claim 1.

16. The method of claim 1, wherein said medical instrument includes at least one marker attached thereto, further comprising ascertaining a spatial position of the medical instrument based on the at least one marker.

17. The method according to claim 1, wherein ascertaining includes concluding that the medical instrument is calibrated if certain areas are within a predetermined tolerance of the pre-calibration data.

18. A device for calibrating a medical instrument, comprising:
- a computing unit having a memory in which pre-calibration data of the medical instrument is stored, wherein the pre-calibration data includes data relevant to the function of the medical instrument;
- at least one first camera for detecting markers attached to the medical instrument; and
- at least one second camera for capturing at least one actual image of the medical instrument, wherein the at least one actual image includes certain areas corresponding to the stored pre-calibration data and the first camera and the second camera are communicatively coupled to the computing unit and exhibit a defined spatial relationship to each other, said spatial relationship determinable by the computing unit,
- wherein the computing unit ascertains whether or not the medical instrument is calibrated based on a comparison between the actual image of the medical instrument and a calculated virtual image, said virtual image based on a position of the markers detected by the first camera.

19. The device according to claim 18, wherein the second camera is connected to at least one marker.

20. The device according to claim 18, further comprising an optical display on which an actual video image of the medical instrument can be represented together with a computer generated image of the medical instrument calculated from the pre-calibration data.

21. A system comprising a device according to claim 18 and the medical instrument which is connected to at least one marker.

22. A device for calibrating a medical instrument, comprising:
- a computing unit having a memory in which pre-calibration data of the medical instrument is stored, wherein the pre-calibration data includes data relevant to the function of the medical instrument; and
- at least one camera for detecting markers attached to the medical instrument and for capturing at least one actual image of the medical instrument, wherein the at least one actual image includes certain areas corresponding to the stored pre-calibration data and the at least one camera is communicatively coupled to the computing unit,
- wherein the computing unit is configured to ascertain whether or not the medical instrument is calibrated based on a comparison between the actual image and a calculated virtual image, said virtual image based on a position of the markers detected by the first camera.

23. The device according to claim 22, wherein the at least one camera comprises a first camera and a second camera, and wherein the first camera is configured to detect the markers, and the second camera is configured to capture the actual image of the medical instrument.

* * * * *